United States Patent
Bulbrook

(10) Patent No.: US 9,968,281 B2
(45) Date of Patent: May 15, 2018

(54) BREATH CONDENSATE COLLECTOR

(71) Applicant: Exhalation Technology Ltd, Norfolk (GB)

(72) Inventor: George Lee Bulbrook, Norfolk (GB)

(73) Assignee: Exhalation Technology Ltd, Norfolk (GB)

( * ) Notice: Subject to any disclaimer, the term of this patent is extended or adjusted under 35 U.S.C. 154(b) by 0 days. days.

(21) Appl. No.: 15/169,891

(22) Filed: Jun. 1, 2016

(65) Prior Publication Data

US 2016/0270693 A1    Sep. 22, 2016

Related U.S. Application Data

(63) Continuation of application No. 12/670,432, filed as application No. PCT/GB2008/001954 on Jun. 6, 2008.

(30) Foreign Application Priority Data

Jul. 24, 2007 (GB) ................... 0714424.9

(51) Int. Cl.
*A61B 5/097* (2006.01)
*A61B 5/00* (2006.01)

(52) U.S. Cl.
CPC ............ *A61B 5/097* (2013.01); *A61B 5/6803* (2013.01); *A61B 2503/40* (2013.01)

(58) Field of Classification Search
CPC .................. G01N 33/497; A61B 5/097; A61B 2010/0087
See application file for complete search history.

(56) References Cited

U.S. PATENT DOCUMENTS

| | | | | |
|---|---|---|---|---|
| 5,465,728 A | * | 11/1995 | Phillips | A61B 5/097 128/204.17 |
| 7,118,537 B2 | * | 10/2006 | Baddour | A61B 5/082 600/532 |
| 2004/0127808 A1 | * | 7/2004 | Vaughan | A61B 5/412 600/532 |
| 2004/0161804 A1 | | 8/2004 | McCash et al. | |
| 2004/0162500 A1 | * | 8/2004 | Kline | A61B 5/097 600/532 |

(Continued)

FOREIGN PATENT DOCUMENTS

| | | |
|---|---|---|
| CA | 2312808 | 6/1999 |
| GB | 2427686 | 1/2007 |
| WO | 95/31721 | 11/1995 |

(Continued)

OTHER PUBLICATIONS

International Search Report for corresponding Patent Application No. PCT/GB2008/001954 dated Sep. 19, 2008.

*Primary Examiner* — Patricia Mallari
*Assistant Examiner* — Michael Catina
(74) *Attorney, Agent, or Firm* — Renner, Otto, Boisselle & Sklar, LLP

(57) ABSTRACT

A breath condensate collector (10) comprising a chamber having a breath inlet port (14) and an outlet port (16); a sample collector, adapted to receive breath from the chamber outlet and having air exhaust means; cooling means (112) to promote in use condensation of vapor from breath entering the sample collector and where collector comprises a partially lidded dish (110).

11 Claims, 5 Drawing Sheets

(56) References Cited

U.S. PATENT DOCUMENTS

2005/0137491 A1    6/2005   Paz et al.
2008/0045825 A1*   2/2008   Melker .................. A61B 5/083
                                                             600/365

FOREIGN PATENT DOCUMENTS

| WO | 02/082977   | 10/2002 |
| WO | 2006/043290 | 4/2006  |
| WO | 2007/001342 | 1/2007  |

* cited by examiner

Figure 1 – Prior Art

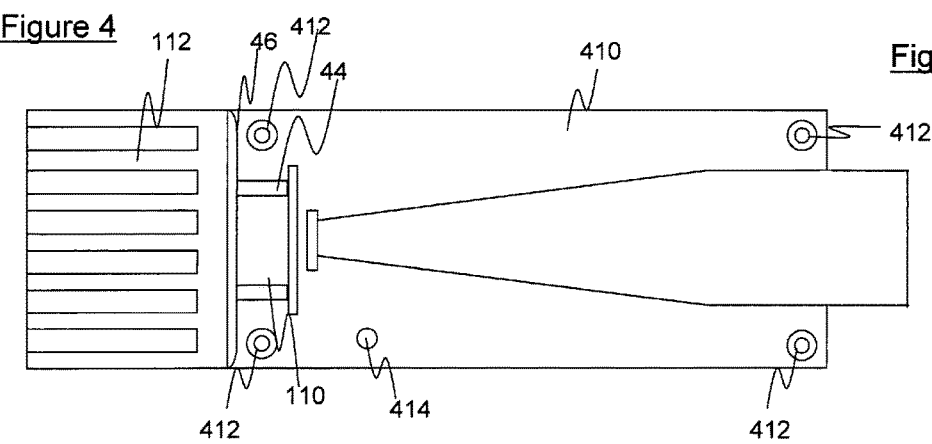
Figure 4
Figure 6
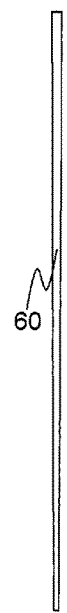
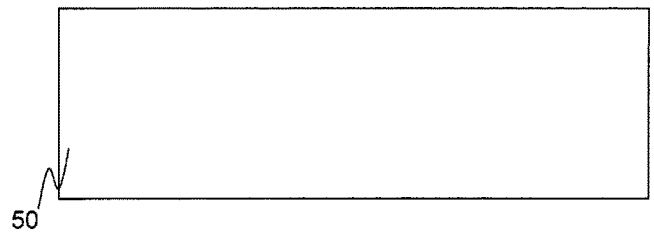
Figure 5

BREATH CONDENSATE COLLECTOR

This application is a continuation of U.S. application Ser. No. 12/670,432 filed Jan. 25, 2010, which is a U.S. National Phase of International Application No. PCT/GB2008/001954 filed Jun. 6, 2008 and published in the English language, which claims priority to United Kingdom Patent Application No. 0714424.9 filed Jul. 24, 2007, which are all hereby incorporated herein by reference in their entirety.

FIELD OF THE INVENTION

This invention concerns apparatus for the collection of breath condensate and also apparatus specifically for collection of breath condensate from animals, especially horses and humans.

BACKGROUND AND PRIOR ART KNOWN TO THE APPLICANT

Breath Condensate collectors are known. For example, application number GB 2427686 discloses, in its broadest aspect:

A breath condensate collector comprising: a chamber having a breath inlet port, an air inlet port and an outlet port; a one-way valve, located in said air inlet port, to allow flow of air into the chamber, whilst resisting flow of air or breath out of the chamber; a sample collector, adapted to receive air from the chamber outlet, and having air exhaust means; cooling means, to promote, in use, condensation of vapour from breath entering the sample collector; and characterised by the feature that the flow path from the breath inlet port to the sample collector is unimpeded by a valve.

Application GB 2427686 also discloses the following prior art:

Determination of the concentration of metabolites present in exhaled breath is useful for a number of clinical indications. One such metabolite is hydrogen peroxide, and elevated levels of this in exhaled breath can be indicative of pulmonary dysfunction. Apparatus for the collection breath condensate are known in themselves. One such device is illustrated in FIG. 1. The device consists essentially of a tube 1 with a side-arm 2. Within the tube are two one-way valves, 3 and 4, located either side of the side arm. The side arm acts as a mouthpiece, and may be specifically shaped to assist sealing by a user's lips. During use, a patient inserts the mouthpiece into their mouth, and is instructed to breathe through their mouth (rather than nose). As they breathe in, the valve arrangement allows air to pass through the lower one-way valve, 4, with the upper valve, 3, remaining closed, as indicated in FIG. 1(a). As they breathe out, the lower valve 4 closes, and the upper valve opens, causing the air to pass through the upper portion of the tube 1. Breath condensate then collects on the inner surface of the tube 1, from where it may be harvested. Cooling may be applied to the outside of the tube, 1, to promote condensation.

In one such type of apparatus, the upper valve 3, is of a so-called "duckbill" configuration—a generally dome-shaped configuration, made of a rubber-like material, and having a slit at the domed end, forming a pair of lip-like structures. This is illustrated in cross-section in FIG. 1. In its relaxed state, the duckbill valve is in a closed configuration. A decreased pressure within the dome of the valve, as would be experienced during inhalation tends to maintain this closed configuration. An increased pressure within the dome, as would be experienced during exhalation against the now closed second valve, 4, causes the valve to open. It is known that, during storage, one-way valves (and especially those of the "duckbill" configuration) tend to stick in their "at rest" state. In consequence, the device may prevent a user from exhaling. Unless rectified by an informed user before use, this phenomenon may cause alarm. Whilst an informed adult user might recognise the problem, and take actions to remedy it, a child may tend to become distressed, or annoyed.

The passage of air through the valve systems also tends to offer some resistance to breathing. For informed and cooperative users, with relatively good lung function, this is usually not problematic, but can become a significant drawback in situations where communication with the patient, or subject, is difficult.

In addition, devices of this nature require the user to consciously breathe through their mouths, rather than through their nose. Again, when used with informed and cooperative users this is usually not problematic, but can become problematic where communication with the patient, or subject, is difficult.

Finally, devices of this nature are relatively complex, and require multiple one-way valves, located within the body of a narrow tube, in order to function. This tends to increase manufacture costs.

All of these problems with current devices become especially heightened in the field of veterinary, and especially equine, healthcare. In these situations, the subject animal is likely to be restless, uncooperative, and easily alarmed. On top of this, meaningful communication is impossible.

Since that invention, it has been discovered that the type of sample collected in conventional collectors usually comprises a mixture of aerosol and true condensate.

None of the current breath condensate collectors facilitates the collection of both types of sample separately.

Both are useful to the analyst, but for different diagnostic purposes. As there is therefore a need for a condensate collector, which makes easy the collection of samples enriched in condensate or aerosol.

In addition, it has been observed that existing breath condensate collection technology can cause problems for those who need to take a quick sample—perhaps for a drug test before a horse race—or those who need to take a sample outside of a well—equipped clinical environment, such as travelling vets.

Of course, such environments present a greater risk of contamination to samples, and the high risk of contamination is something which previous examples of the art have suffered, perhaps due to their complexity, or perhaps due to the difficulties presented to the person who would try to clean them.

It is an object of the present invention to attempt to provide a solution to these and other problems.

SUMMARY OF THE INVENTION

In its broadest aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector and where the sample collector comprises a partially lidded dish.

Samples will collect in both the chamber and the sample collector. Samples in the chamber will be condensate rich; Samples in the sample collector will be aerosol rich.

By partially lidded dish, it is meant that the area of the opening of the dish is less than the cross sectional area of the dish's interior immediately beneath the opening.

The partially lidded dish is advantageous over fully open receptacles in that when air flows into the dish, it will not immediately deflect back out of the dish again. Instead, a large proportion of the breath will hit the inside of the lid. Unable to vacate the sample collector, it is caused to swirl around. Such swirling will lead to the deposition of more condensate and aerosol from the breath, into the dish itself. This gives a larger sample, and may also have more diagnostic value, since parts of the sample more easily carried by the air will be more likely to settle in the dish.

The partially lidded dish is further advantageous in relation to open dishes in that it provides a smaller target for contamination.

The invention is further advantageous in that both the chamber and the sample collector may be used to collect condensate. In other words, the invention provides a breath collection apparatus, having two sample collection recipients: one with a collection surface substantially parallel to the flow of breath for collection of a sample primarily comprising breath condensate and a second recipient with a collection surface substantially perpendicular to the flow of breath (such that the breath flow impinges on the collection surface thereby causing breath borne aerosol droplets to impact on the collection surface) for collection of sample containing condensate and enriched with breath-borne aerosol. Given that it has been proven that each sort of condensate has its own value, this may prove particularly useful in cases where a comparative study is desirable, and further or alternatively in situations where tests on both samples may advantageously be taken, or further where the right test has yet to be ascertained, and therefore either or both samples may prove useful.

Still more advantageous is the fact that both samples may be collected almost simultaneously, via one exhalation from the subject. This is quicker, and this speed is useful when the very act of procuring the sample is putting an animal under stress.

In any aspect of invention, it is preferable that the chamber is cylindrical.

It is advantageous to have a cylindrical chamber because it is easier to scrape the condensate out of a cylinder—none of it will be stuck in corners, or at the intersection between planes, as would happen with a rectangular or a pyramidal chamber. As has been mentioned, the condensate collected in the cylinder has particular diagnostic value and as such it is especially important that collection should be made easier.

For the same reason, it is easier to clean cylindrical tubes. This is particularly important where tests may be for a contagious disease, because hygiene will be paramount in those circumstances.

Also, in any aspect of invention, it is preferable that at least a part of the chamber is tapered.

The tapered chamber is particularly advantageous in that it disrupts air passing down it, creating turbulent rather than laminar flow conditions. This has two subsidiary advantages in itself.

The first is that the turbulence tends to cause more condensate and aerosol to drop out of the air.

The second is that turbulent flow leads to the formation of a thinner boundary layer on the inside of the tube, which itself increases condensation.

Also, in any aspect of invention, it is preferable that at least a part of the inner surface of the chamber comprises a hydrophobic material.

This is particularly advantageous in that hydrophobic material will encourage the condensate to form droplets, rather than spread out and "wet" the surface. This will lead to faster and more effective collecting of condensate from the chamber.

It is also advantageous in that the provision of a hydrophobic surface will tend to aid the flowing of the condensate from chamber to sample collector, especially when held at such an angle as to encourage such flow.

Also, in any aspect of invention, it is preferable that at least part of the inner surface of the sample collector comprises a hydrophobic material.

This is particularly advantageous in that hydrophobic material will encourage the condensate to form droplets, rather than spread out and "wet" the surface. This will lead to faster and more effective collecting of condensate from the sample collector.

Also, in any aspect of invention, it is preferable that the cooling means comprises a Peltier device.

The provision of a Peltier device is advantageous, in that it provides a manner of controlling the temperature of a sample collector placed adjacent to it, to a high degree of precision.

A second advantage is that the Peltier device will tend to cool for longer than other means, such as a gel wrapper or the provision of cold-retentive materials.

The most important advantage of all is that unlike the gel wrapper and the cold retentive materials, the Peltier device provides its own means for displacing heat—it is integral to the condensate collector and is not reliant on external sources for cooling. This will be of particular utility to the travelling veterinarian, for example, who may need to take samples of condensate on an ad hoc basis, and away from the external refrigeration means that would be required to cool other cooling means to the requisite temperature.

Also, in any aspect of invention, it is preferable that the breath condensate collector further comprises a wand.

It is particularly advantageous to include a wand in the apparatus, as the wand may be used to collect condensate from the chamber and the sample collector.

Also, in any aspect of invention, it is preferable that the wand is tapered.

The wand will be of advantage in that when held correctly, the taper will encourage the condensate to run along the wand and form at the tip, allowing for ease of collection.

Also, in any aspect of invention, it is preferable that the wand is resiliently deformable.

Advantageously, the resiliently deformable wand will deform to match the profile of the inside of the condensate collector, allowing the wand to scrape or wipe in a quicker and more comprehensive fashion, covering more of the surface area per motion.

Also, in any aspect of invention, it is preferable that the surface of the wand is hydrophobic.

Making the surface of the wand hydrophobic will encourage the formation of droplets on the wand, which will enhance the efficiency with which a large droplet can be formed at the end of the wand.

That the wand is hydrophobic will further encourage the travel of the droplets to the tip of the wand.

In another aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector and wherein the chamber is cylindrical.

In another aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector and wherein the chamber is tapered In another aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector and wherein the chamber comprises a hydrophobic material.

In another aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector and wherein at least part of the inner surface of the sample collector comprises a hydrophobic material.

In another aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector and wherein the cooling means comprises a Peltier device.

In another aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector; and a wand.

In another aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector; and a tapered wand.

In another aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector; and a resiliently deformable wand.

In another aspect, the invention comprises a breath condensate collector comprising a chamber having a breath inlet port and an outlet port; a sample collector, adapted to receive breath from the chamber outlet and having air exhaust means; cooling means to promote in use condensation of vapour from breath entering the sample collector; and a hydrophobic wand.

BRIEF DESCRIPTION OF THE DRAWINGS

The invention will be illustrated by the accompanying drawings, in which:

FIG. 4 shows a plan view of the device.
FIG. 5 shows a plan view of a disposable tube.
FIG. 6 shows an elevational view of a wand.

DESCRIPTION OF PREFERRED EMBODIMENTS

Figure 1:
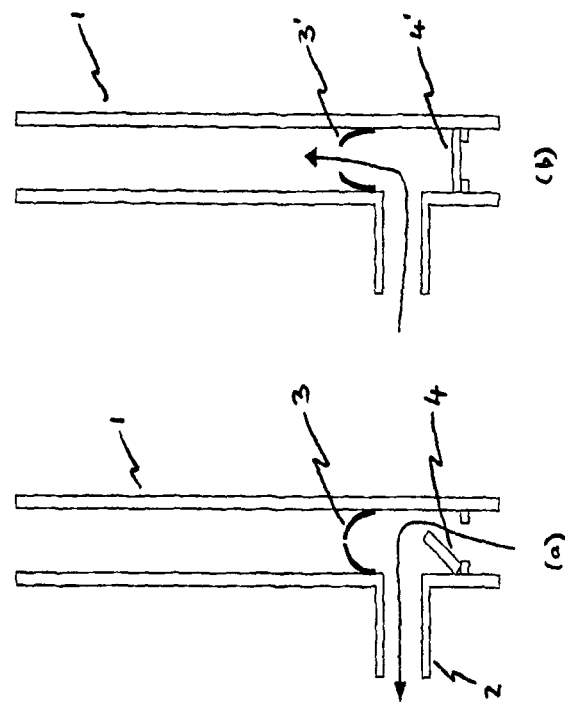
FIG. 1 shows a cross sectional view of the prior art.
Figure 2:
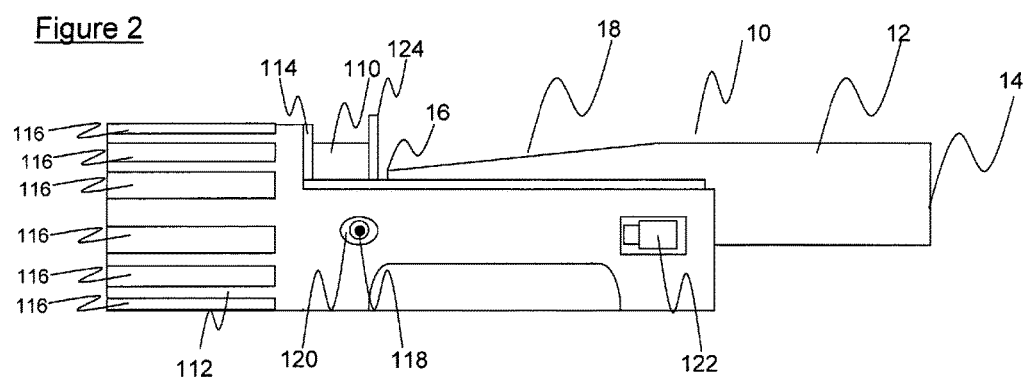
FIG. 2 shows a side elevation view of a breath collection device.

FIG. 2 shows a breath condensate collector generally indicated by 10. This embodiment is made largely of polypropylene and aluminium, both of which are robust and easy to clean. The device 10 has a chamber 12, with a breath inlet port 14 and an outlet port 16. In the present embodiment, the chamber 12 is cylindrical and has a circular cross section. The chamber also has a tapered portion 18. Other embodiments need not be cylindrical. Equally, the chamber 12 may be entirely tapered or not tapered at all. A particularly advantageous shape for the chamber 12 is a frusto-conical shape or similar, since I resiliently deformable wand may easily be designed to match the profile of the taper of the inner surface of such a chamber 12.

In this embodiment, the inlet port 14 is furthest away from the sample collector, which is a partially lidded dish 110, while the outlet port 16 is near to the partially lidded dish 110. The chamber 12 fits frictionally inside the breath condensate collector 10. It may alternatively be held in place by supplementary attachment means. In this embodiment, the chamber 12 is removable.

In this embodiment, the entire inside of the chamber 12 is coated with a hydrophobic material. This may be a material of the polytetrafluoroethylene (PTFE) family such as Teflon™, made by E. I. du Pont de Nemours and Company of 1007 Market St. Wilmington, Del. 19898, USA, or comprise a siliconised surface or any other material or combination of materials known to the skilled man. The material may be part of the chamber 12 itself or the chamber 12 may be made from it. It may cover all or part of the inside of the chamber 12.

The chamber 12, may be partially or entirely transparent.

In this embodiment, the chamber 12 is reusable and it is made of plastics. It is so fashioned that it may be easily cleaned between uses. Reusable chambers may also be fashioned of stainless steel or composite materials. Alternatively, disposable cardboard or plastics chambers may be appropriate.

Figure 3:
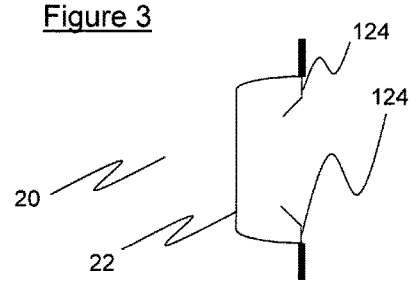
FIG. 3 shows a cross-sectional side view of a partially lidded dish.

FIG. 3 shows a partially lidded dish 110. The dish comprises a dish portion 22 and a partial lid portion 124 defining an aperture. These two portions 22 124 are inseparable in some embodiments. In others, the partial lid portion 124 may be detached from the dish portion 22. In this embodiment, the entire inside of the dish 110 is coated with a hydrophobic material. This may be a material of the polytetrafluoroethylene (PTFE) family, or comprise a siliconised surface or any other material or combination of materials known to the skilled man. In other embodiments, it need not be a coating—the dish 110 can be made from the material. Equally, it is not necessary that the entire surface be made or coated in a hydrophobic material—only part of it may be coated. The partially lidded dish feature is also of particular advantage over the syringe used in GB2427686 in that the partially lidded dish has a smaller surface area than the syringe and is therefore easier to cool. In this embodiment the partial lid portion 24 is transparent. The dish portion 22 is made of aluminium, in order to effect good heat transfer.

Returning to FIG. 2, there is illustrated an embodiment of the partially lidded dish, 110, placed in the condensate receiving position within the breath condensate collector 10. It is inside a recess (not shown). It is retained there by any retention means known to the skilled man, although a frictional fit may suffice. The partially lidded dish 110 is positioned so that its aperture faces the outlet port 16. In circumstances where the breath condensate collector 10 is positioned in such a way that its longest axis runs along a substantially horizontal plane, the partial lid feature 24 will serve to stop the condensate from coming out of the aperture, because the inside of the partial lid feature 24 forms a reservoir with the inner surface of the partially lidded dish 110.

The ideal placement of the partially lidded dish 110 in relation to the outlet port 18, is to have each facing the other, the outlet port 16 being so sized that condensate travelling down it will be directed into the partially lidded dish 110 and so placed so as to be substantially aligned with the aperture formed by the partial lid. In this embodiment there is a distance of about 2 mm between the outlet port 16 and the partial lid portion 124. Other placements are envisaged, but this is the optimal placement. If the outlet port 16, was inside the dish 110, the flow of air into the dish 110 would serve to dry any condensate collected, thus robbing it of at least part of its diagnostic value. If the outlet port 16 was further away from the partially lidded dish 110, there would be two problems. The first would be that of improperly directed condensate, which may at least be messy, and at most the possible carrier of infectious matter or otherwise dangerous. The second would be that the flow of air would be prone to making a whistling sound upon contact with the partially lidded dish 110. In embodiments where the collector is being used to collect condensate from an animal such as a horse, the whistling may startle or otherwise disconcert the horse, thus hampering the collection of condensate or endangering the people collecting it.

The collector 10 further features cooling means 112 to promote in use condensation of vapour from breath entering the collection condensate vessel. In this embodiment, said cooling means 112 comprises a Peltier device, having a cooling surface 114 and heat dissipating fins 116 of which six can be seen. The cooling surface 114 is so arranged as to be in operable communication with the partially lidded dish 110 on a flat or curved plane, and may follow the profile of the partially lidded dish 110.

The device is powered by conventional means (not shown), and is rechargeable. It may be attached to a power source via a recharge point 118 which in this embodiment is situated in a recess 120. The employment of a Peltier device 112 dispenses with the need for external cooling means, making it particularly useful for the travelling vet, or someone who is otherwise without separate refrigeration means. The Peltier device 112 is operated via an on/off switch 122, but may alternatively be operated by a switch actuated by the placement or removal of the lidded dish 110 in the recess (not shown).

In the alternative, other cooling means, such as a pre-cooled metallic element or a cooling jacket may be substituted.

FIG. 4 shows the invention 10. It has a partially lidded dish 110, in a recess 44. In this embodiment, it can clearly be seen that the recess 44 is so fashioned as to bring the partially lidded dish 110, into abutment with the cooling surface 46 of the Peltier device 112. In this embodiment, the fascia 410 is transparent and removable, being attached by screws 412. This increases the visibility of parts under the fascia 410 and allows easy cleaning of the device. The device also has an LED 414, which in this embodiment shines green when the device is on, and flashes red when it is running out of power.

FIG. 5 shows, for human use, a disposable, cylindrical, open-ended tube made, for example, of cardboard, which may be connected to the inlet port 14 of a device 10 to facilitate a user blowing into a device without ever having to place the device itself into the mouth, with evident hygiene benefits.

FIG. 6 shows a wand, 60. In this embodiment, the wand 60 is tapered, resiliently deformable and of a hydrophobic material, although in other embodiments, it might feature only a selection of these features, or none at all. In this embodiment, the dimensions of the wand are optimised so that it can best be used to remove condensate attached to the sides of a chamber, being operated by the user with a motion which could be described as "scraping" or "wiping"

This embodiment of the wand 60 has a deformation profile of such attributes that when, in use, force is applied to the wand 60 it deforms in such a way as to mimic the curvature of the chamber or sample collector of the device. This will enable the wand 60 to be used to scrape the condensate more quickly and effectively. Having got the condensate onto the wand 60, the provision of hydrophobic material encourages the condensate to form in beads on the wand 60. The taper will then encourage droplets on a wand 60 which is held so that the thin end is pointing substantially downwards to travel towards the tip.

Figure 7:
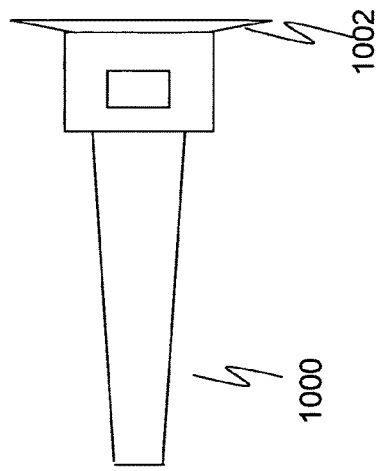
FIG. 7 shows an elevational view of a chamber.

FIG. 7 shows a chamber 70. It has an open-ended frusto-conical profile, so as to work synergistically with a wand.

Figure 8:
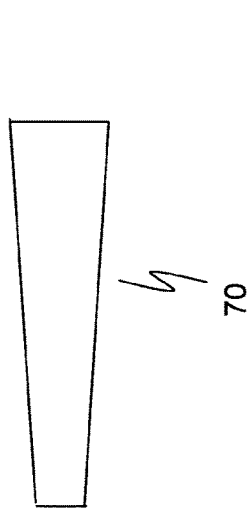
FIG. 8 shows a further elevational view of a chamber.

FIG. 8 shows another chamber 80. It has a flange 82, allowing for the attachment of further items, such as, for example, filtration devices or deformable plastic masks.

Figure 9:
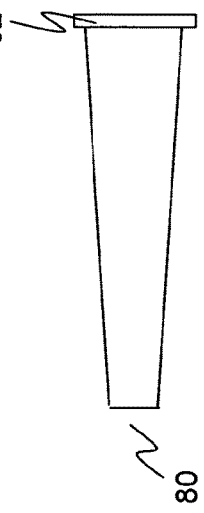
FIG. 9 shows a further elevational view of a chamber.

FIG. 9 shows a further chamber 90. It is cylindrical and open-ended. It has a raised, tapered inlet 92 which may act as a flange.

Figure 10:
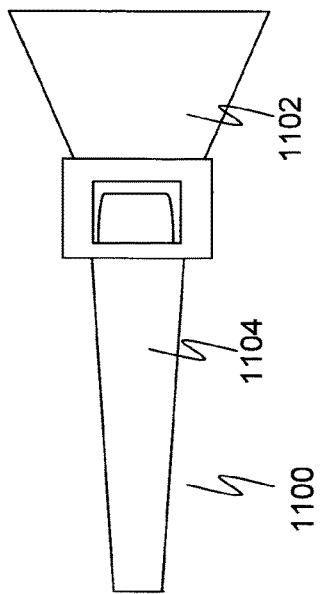
FIG. 10 shows a further elevational view of a chamber.

FIG. 10 shows a still further chamber 1000. It features attachment means 1002 which in this example is a flange portion, but alternative means may be provided. For veterinary use, the chamber 1000 may be connected to a mask, adapted to fit over one or more nostrils of an animal. The mask (not shown) is specifically adapted to fit over a horse's nostril. The mask has generally cylindrical symmetry. Known devices for breath collection rely on a user putting the device in their mouth and breathing out, into the device, through the mouth rather than the nose. For veterinary use, it is not possible to communicate with animals to make them breathe through the mouth, and the use of the device in an animal's mouth poses risk of biting either the device, or the supervising veterinarian. The provision of a mask adapted to receive exhaled breath from the nostrils overcomes this problem. For some animals, it is envisaged that a suitable mask might fit over both the nose and the mouth.

Figure 11:
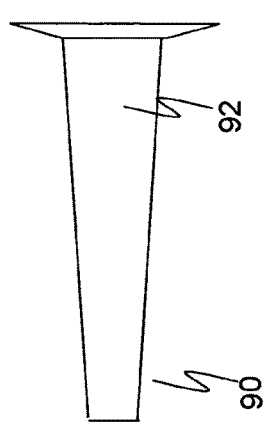
FIG. 11 shows a further elevational view of a chamber.

FIG. 11 shows a still further chamber 1100 with an integral mask 1102 of the type described above. In this embodiment, the mask 1102 is resiliently deformable and designed so as to fit the contours of an animal's nostril and provide an airtight seal. The mask 1102 is resiliently deformable so that if more than one attempt is required to fit the mask over the nostril, the mask will spring back into shape between attempts. The mask may also, therefore, be used again with a different animal.

Figure 12:
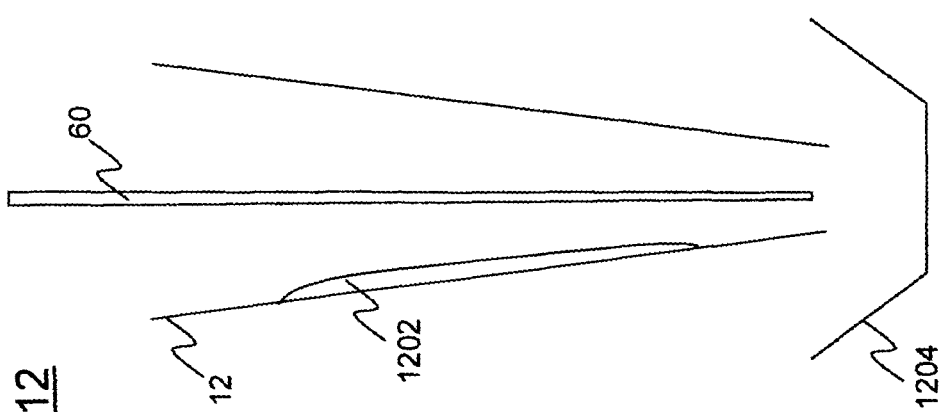
FIG. 12 shows a cross sectional view of a chamber and a dish, illustrating a wand in use.

FIG. 12 shows a method by which a chamber 12, shown here in cross-section, is wiped or scraped of condensate 1202 using a wand 60. This is the second method of collection possible with this device, the first method being that outlined above, wherein the subject breathes down the chamber 12 and into the partially lidded dish 110. This second method facilitates collection of condensate with a lower aerosol quotient, whereas the first method facilitates collection of condensate with a higher aerosol quotient. Also shown is a dish 1204. Here the chamber 12 has been detached from the device 10. The wand 60 is placed inside the chamber 12.

Figure 13:
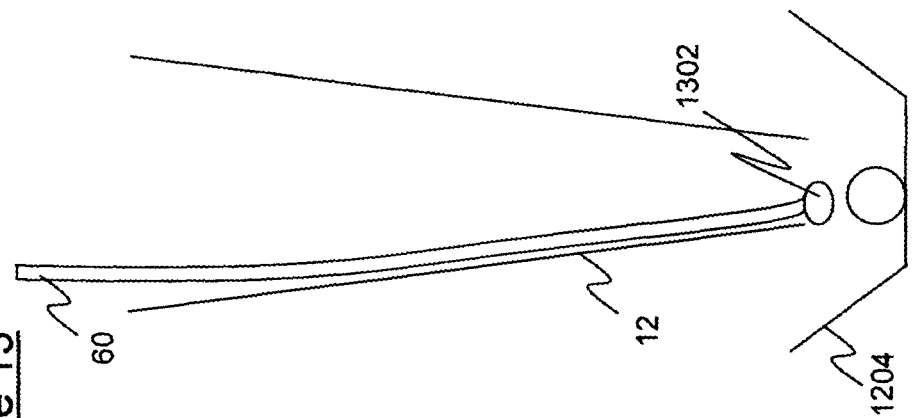
FIG. 13 shows a cross sectional view of a chamber and a dish, illustrating a wand in use.

FIG. 13 shows a wand 60 being manipulated (manipulation means not shown) so that it deforms to form a substantial contact with the inner wall of the chamber 12. Condensate 1202 lining the chamber 12 will be forced off it by the contact of the wand 60 as it is wiped around the inside of the chamber and will be manipulated into the dish 1204. It will be encouraged to flow down the wand 60 if the wand 60 is tapered and/or has a hydrophobic surface. The condensate 1202 will tend to form a droplet 1302, which when force is applied to it may drop into a conveniently placed dish 1204.

Clearly the chamber 12 need not be detached from the device 10 in order for condensate to be collected.

It is possible to use the chamber 12 and wand 60 configuration on its own (i.e. without the sample collector) to collect condensate, and embodiments may therefore be envisaged comprising the chamber 12 and the wand 60.

The invention claimed is:

1. A breath condensate collector comprising:
    a longitudinally extending chamber having a longitudinal axis and at opposite ends a breath inlet port and an outlet port;
    a sample collector comprising a partially lidded dish having an open end and a closed end opposite the open end, the closed end forming a bottom surface of the partially lidded dish, the closed end and the open end each being longitudinally aligned with the outlet port of the chamber along the longitudinal axis to receive breath from the chamber outlet such that the closed end of the partially lidded dish is disposed in the path of the breath passing longitudinally from the chamber outlet port and into the partially lidded dish through the open end of the partially lidded dish, and the sample collector having air exhaust proximate the open end of the partially lidded dish; and
    a cooling element in thermal communication with the bottom surface of said partially lidded dish, to promote, in use, condensation of vapour from breath entering the sample collector.

2. A breath condensate collector according to claim 1, wherein the chamber is cylindrical.

3. A breath condensate collector according to claim 1, wherein at least a part of the chamber is tapered along the longitudinal axis that intersects the closed end of the partially lidded dish.

4. A breath condensate collector according to claim 1, wherein at least a part of the inner surface of the chamber comprises a hydrophobic material.

5. A breath condensate collector according to claim 1, wherein at least part of the inner surface of the sample collector comprises a hydrophobic material.

6. A breath condensate collector according to claim 1, wherein the cooling element comprises a Peltier device.

7. A breath condensate collector according to claim 1, further comprising a wand.

8. A breath condensate collector according to claim 7, wherein the wand is tapered.

9. A breath condensate collector according to claim 7, wherein the surface of the wand is hydrophobic.

10. A breath condensate collector according to claim 1, in which said sample collector is spaced apart from the outlet port of said chamber, and said outlet port is aligned with the aperture formed by a partial lid.

11. A breath condensate collector according to claim 1, wherein the cooling element contacts the closed end of the partially lidded dish.

* * * * *